US012687546B2

(12) United States Patent
Nakamura et al.

(10) Patent No.: US 12,687,546 B2
(45) **Date of Patent: *Jul. 21, 2026**

(54) REAGENT KIT, MEASUREMENT KIT, AND MEASUREMENT METHOD

(71) Applicant: FUJIFILM Corporation, Tokyo (JP)

(72) Inventors: Kazuhiro Nakamura, Ashigarakami-gun (JP); Ryo Ouchi, Ashigarakami-gun (JP); Takeru Shigemura, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 1134 days.

This patent is subject to a terminal disclaimer.

(21) Appl. No.: 17/390,010

(22) Filed: Jul. 30, 2021

(65) Prior Publication Data

US 2021/0356474 A1 Nov. 18, 2021

Related U.S. Application Data

(63) Continuation of application No. PCT/JP2020/003296, filed on Jan. 30, 2020.

(30) Foreign Application Priority Data

Jan. 31, 2019 (JP) ................................ 2019-015663

(51) Int. Cl.
*G01N 33/68* (2006.01)
*B82Y 5/00* (2011.01)
(Continued)

(52) U.S. Cl.
CPC ..... *G01N 33/6839* (2013.01); *G01N 21/6428* (2013.01); *G01N 33/543* (2013.01);
(Continued)

(58) Field of Classification Search
CPC ........... G01N 33/6839; G01N 21/6428; G01N 33/543; G01N 2021/6439; B82Y 5/00; B82Y 35/00
See application file for complete search history.

(56) References Cited

U.S. PATENT DOCUMENTS

| | | | |
|---|---|---|---|
| 5,403,716 | A | 4/1995 | Matsuzawa et al. |
| 2009/0130696 | A1 | 5/2009 | Murphy et al. |

(Continued)

FOREIGN PATENT DOCUMENTS

| | | | |
|---|---|---|---|
| CN | 105393119 A | | 3/2016 |
| CN | 105675879 A | * | 6/2016 |

(Continued)

OTHER PUBLICATIONS

Koley, Dipankar, Triton x-100 concentration effects on membrane permeability of a single HeLa cell by scanning electrochemical microscopy (SECM), Aug. 2010, Proceedings of the National Academy of Sciences of the United States of America, 107(39), pp. 16783-16787. Retrieved Nov. 26, 2024 (Year: 2010).*

(Continued)

*Primary Examiner* — Charles Capozzi
*Assistant Examiner* — Alex Ramirez
(74) *Attorney, Agent, or Firm* — Birch, Stewart, Kolasch & Birch, LLP

(57) ABSTRACT

An object of the present invention is to provide a reagent kit, a measurement kit, and a measurement method for measuring serum amyloid A, which enable simple and rapid measurement of serum amyloid A by promoting dissociation of the serum amyloid A from HDL and carrying out an antigen-antibody reaction. According to the present invention, provided is a reagent kit for measuring serum amyloid A, including first particles having a label and modified with a first binding substance having a property of specifically (Continued)

binding to serum amyloid A, at least one nonionic surfactant having an HLB value of 17 to 20, which is defined by (inorganicity value/organicity value)×10, and a molecular weight of 1000 or less, and a buffer capable of adjusting a pH of a reaction solution to be in a range of 5.5 to 7.0 or a range of 8.5 to 9.0.

19 Claims, 2 Drawing Sheets

(51) Int. Cl.
*B82Y 35/00* (2011.01)
*G01N 21/64* (2006.01)
*G01N 33/543* (2006.01)

(52) U.S. Cl.
CPC ................. *B82Y 5/00* (2013.01); *B82Y 35/00* (2013.01); *G01N 2021/6439* (2013.01)

(56) References Cited

U.S. PATENT DOCUMENTS

| | | | | |
|---|---|---|---|---|
| 2009/0261269 | A1 | 10/2009 | Horii et al. | |
| 2011/0091993 | A1 | 4/2011 | Matsuo et al. | |
| 2015/0038355 | A1 | 2/2015 | Tan et al. | |
| 2016/0069909 | A1* | 3/2016 | Nakamura | G01N 33/582 436/501 |
| 2018/0372737 | A1 | 12/2018 | Kasagi et al. | |
| 2020/0408773 | A1 | 12/2020 | Nakamura et al. | |
| 2021/0148932 | A1 | 5/2021 | Asahi et al. | |
| 2021/0356458 | A1 | 11/2021 | Nakamura et al. | |
| 2021/0356474 | A1 | 11/2021 | Nakamura et al. | |

FOREIGN PATENT DOCUMENTS

| | | | | |
|---|---|---|---|---|
| CN | 105929173 | A | | 9/2016 |
| CN | 106053862 | A | | 10/2016 |
| CN | 106198961 | A | | 12/2016 |
| CN | 106353507 | A | | 1/2017 |
| CN | 106568978 | A | | 4/2017 |
| CN | 107015004 | A | * | 8/2017 |
| CN | 107167597 | A | | 9/2017 |
| EP | 3 767 293 | A1 | | 1/2021 |
| EP | 3 767 294 | A1 | | 1/2021 |
| JP | 8-178921 | A | | 7/1996 |
| JP | 9-104699 | A | | 4/1997 |
| JP | 10-282105 | A | | 10/1998 |
| JP | 2006-17745 | A | | 1/2006 |
| JP | 2009-537018 | A | | 10/2009 |
| JP | 2010-190880 | A | | 9/2010 |
| JP | 2016-57145 | A | | 4/2016 |
| WO | WO 92/12429 | A1 | | 7/1992 |
| WO | WO2009/116268 | A1 | | 9/2009 |
| WO | WO2017/009926 | A1 | | 1/2017 |
| WO | WO 2017/150518 | A1 | | 9/2017 |
| WO | WO 2019/004168 | A1 | | 1/2019 |

OTHER PUBLICATIONS

Fisher scientific, Triton X-100, Thermo Scientific Chemicals, retrieved Nov. 26, 2024 from: https://www.fishersci.ca/shop/products/triton-x-100-thermo-scientific/p-3208665 (Year: 2024).*

Japanese Notice of Reasons for Refusal for corresponding Japanese Application No. 2020-569705, dated Mar. 29, 2022, with an English translation.

International Preliminary Report on Patentability and Written Opinion of the International Searching Authority (Forms PCT/IB/326, PCT/IB/373, and PCT/ISA/237) for International Application No. PCT/JP2020/003296, dated Aug. 12, 2021, with English translation of the Written Opinion.

International Search Report (Form PCT/ISA/210) for International Application No. PCT/JP2020/003296, dated Mar. 17, 2020, with English translation.

Extended European Search Report for corresponding European Application No. 20749085.5, dated Feb. 16, 2022.

Chinese Office Action and Search Report for Chinese Application No. 201980019594.1, dated Feb. 24, 2023, with an English translation.

Chinese Office Action and Search Report for Chinese Application No. 201980019624.9, dated Feb. 25, 2023, with English translation.

Chinese Office Action for Chinese Application No. 201980019624.9, dated Jan. 15, 2024, with English translation.

Chinese Office Action for Chinese Application No. 201980019624.9, dated Nov. 4, 2023, with English translation.

European Communication pursuant to Article 94(3) EPC for European Application No. 19766913.8, dated May 23, 2024.

European Communication pursuant to Article 94(3) EPC for European Application No. 19768171.1, dated May 22, 2024.

Extended European Search Report for European Application No. 19766913.8, dated Apr. 16, 2021.

Extended European Search Report for European Application No. 19768171.1, dated Apr. 16, 2021.

Extended European Search Report for European Application No. 20747986.6, dated Jan. 26, 2022.

International Preliminary Report on Patentability and Written Opinion of the International Searching Authority (Forms PCT/IB/326, PCT/IB/373, and PCT/ISA/237) for International Application No. PCT/JP2020/003297, dated Aug. 12, 2021, with an English translation.

International Preliminary Report on Patentability and Written Opinion of the International Searching Authority (Forms PCT/IB/373, PCT/ISA/237 and PCT/IB/326) for International Application No. PCT/JP2019/010920, dated Oct. 1, 2020, with an English translation.

International Preliminary Report on Patentability and Written Opinion of the International Searching Authority, with an English translation (forms PCT/IB/373, PCT/ISA/237 and PCT/IB/326), dated Oct. 1, 2020, for International Application No. PCT/JP2019/010921.

International Search Report (Form PCT/ISA/210) for International Application No. PCT/JP2020/003297, dated Mar. 17, 2020, with an English translation.

International Search Report (Forms PCT/ISA/210 and PCT/ISA/220) for International Application No. PCT/JP2019/010920, dated Jun. 11, 2019, with an English translation.

International Search Report (forms PCT/ISA/210 and PCT/ISA/220), dated Jun. 11, 2019, for International Application No. PCT/JP2019/010921, with an English translation.

Japanese Notice of Reasons for Refusal for Japanese Application No. 2020-506679, dated Mar. 30, 2021, with an English translation.

Japanese Notice of Reasons for Refusal for Japanese Application No. 2020-506680, dated Mar. 30, 2021, with an English translation.

Japanese Notice of Reasons for Refusal for Japanese Application No. 2020-569706, dated Mar. 29, 2022, with an English translation.

Privé, "Detergents for the stabilization and crystallization of membrane proteins," Methods, vol. 41, 2007, pp. 388-397.

Saile et al., "Enzyme-Linked Immunosorbent Assay for Serum Amyloid A Apoliprotein with Use of Specific Antibodies against Synthetic Peptides," Clinical Chemistry, vol. 34, No. 9, 1988, pp. 1767-1771.

Tamamoto, "Cat Inflammation Marker," The Journal of the Hokkaido Veterinary Medical Association, vol. 58, No. 11, Nov. 10, 2014, pp. 539-543.

U.S. Notice of Allowance for U.S. Appl. No. 17/021,671, dated Aug. 1, 2024.

U.S. Notice of Allowance for U.S. Appl. No. 17/021,671, dated May 3, 2024.

U.S. Notice of Allowance for U.S. Appl. No. 17/021,671, dated Oct. 9, 2024.

U.S. Office Action for U.S. Appl. No. 17/021,168, dated Sep. 12, 2024.

U.S. Office Action for U.S. Appl. No. 17/021,168, dated Mar. 27, 2024.

U.S. Office Action for U.S. Appl. No. 17/021,671, dated Jul. 25, 2023.

(56) References Cited

OTHER PUBLICATIONS

U.S. Office Action for U.S. Appl. No. 17/021,671, dated Nov. 21, 2023.
U.S. Office Action for U.S. Appl. No. 17/389,675, dated Feb. 25, 2025.
U.S. Office Action for U.S. Appl. No. 17/389,675, dated Sep. 16, 2024.
Xia et al., "Immunoassay for serum amyloid A using a glassy carbon electrode modified with carboxy-polypyrrole, multiwalled carbon nanotubes, ionic liquid and chitosan," Microchim Acta, vol. 182, 2015, pp. 1395-1402.
U.S. Office Action for U.S. Appl. No. 17/389,675, dated Oct. 1, 2025.
U.S. Office Action for U.S. Appl. No. 17/389,675, dated Jan. 23, 2026.
U.S. Office Action for U.S. Appl. No. 17/389,675, dated Jun. 10, 2026.

* cited by examiner

REAGENT KIT, MEASUREMENT KIT, AND MEASUREMENT METHOD

CROSS-REFERENCE TO RELATED APPLICATIONS

This application is a Continuation of PCT International Application No. PCT/JP2020/003296 filed on Jan. 30, 2020, which claims priority under 35 U.S.C § 119(a) to Japanese Patent Application No. 2019-015663 filed on Jan. 31, 2019. Each of the above application(s) is hereby expressly incorporated by reference, in its entirety, into the present application.

BACKGROUND OF THE INVENTION

1. Field of the Invention

The present invention relates to a reagent kit for measuring serum amyloid A, a measurement kit for serum amyloid A, and a measurement method for serum amyloid A in a biological sample.

2. Description of the Related Art

In the related art, a fluorescence detection method has been widely used as a highly sensitive and easy measurement method in biomeasurement or the like. The fluorescence detection method is a method of confirming the presence of a detection target substance by irradiating a sample considered to contain the detection target substance, which is excited by light having a specific wavelength and emits fluorescence, with excitation light having the specific wavelength and detecting the fluorescence during the irradiation. Further, in a case where the detection target substance is not a fluorophore, a method of bringing a substance that specifically binds to a detection target substance labeled with a fluorescent dye into contact with a sample and detecting fluorescence in the same manner as described above to confirm the presence of the binding, that is, the detection target substance has also been widely used.

Further, in such a fluorescence detection method, a method of using an effect of enhancing the electric field by plasmon resonance in order to improve the sensitivity has been suggested in JP2010-190880A and the like. This method is a method in which a predetermined region on a transparent support comprises a sensor chip provided with a metal layer in order to generate plasmon resonance, excitation light is incident at a predetermined angle greater than or equal to a total reflection angle to an interface between the support and the metal film from a surface side of the support opposite to a metal layer forming surface, surface plasmon is generated in the metal layer by the irradiation with the excitation light, and fluorescence is enhanced due to the effect of enhancing the electric field to improve the signal-to-noise (S/N) ratio.

Serum amyloid A (also noted as SAA) is a protein having a molecular weight of approximately 11600 with extremely high hydrophobicity and has a property in which the concentration in the blood is sharply increased in a case where various stresses such as infections, tumors, traumas, and the like are added to a living body and thus inflammation is caused by these stresses. Therefore, the concentration of SAA in blood is frequently measured by an immunological measurement method as an inflammatory marker used to know the degree of inflammation.

However, it is known that most of SAA is typically associated with high-density lipoprotein (HDL) in blood, probably because of high hydrophobicity of SAA. An antigenic determinant of SAA is hidden in a portion inside the lipoprotein which is not in contact with the outside. Accordingly, the antigenic determinant may not be able to react with the antibody as it is. Therefore, a pretreatment for exposing the hidden antigenic determinant is required in the immunological measurement in many cases. For example, WO92/12429A describes that 2 to 15% by weight of a nonionic surfactant having a hydrophilic-lipophilic balance (HLB) value of 12 or greater is blended according to a method of measuring tissue factor apoprotein.

Further, typically in a quantitative measurement method based on an antigen-antibody reaction, the rare presence of a specimen having a measurement value that is greatly deviated from a quantitative value acquired by a control method (hereinafter, a deviation specimen) is often a problem. The problems of the deviation specimens include a problem in that the correlation coefficients between the measurement values of a plurality of specimens and the quantitative values acquired by the control method are deviated from 1 (deterioration of the correlation with the control method) and a problem of a high-value deviation (which may be a factor of a doctor's misdiagnosis) due to one deviation specimen (particularly deviated on a high value side). The causes of dissociation may be the same as or different from each other depending on the individual deviation specimens. As an example, WO2017/150518A describes that deviation from the control method occurs due to a substance such as an anti-BSA antibody that nonspecifically crosslinks BSA bound onto a test area as a blocking agent and BSA bound onto a side of fluorescent particles in paragraph 0063. WO2017/150518A describes that a method of replacing a part of the blocking agent on the surface of each fluorescent particle with an anti-CRP antibody which is a dummy antibody from BSA is a powerful improvement method for the deviation specimen.

SUMMARY OF THE INVENTION

Based on the description of WO92/12429A, it is evident that serum amyloid A is released from a state of association with HDL due to a surfactant treatment and thus a reaction site is exposed to the outside. However, there is a problem in that the antigen-antibody reaction is strongly suppressed while dissociation from HDL proceeds and the signal intensity is significantly reduced, in a case where 2% to 15% by weight of a nonionic surfactant is added to a measurement system according to a fluorescence detection method (SPF method) by surface plasmon excitation as described in WO92/12429A.

Although the improvement method described in WO2017/150518A is effective, specimens in which deviation cannot be prevented even by such a method are present, and thus it is desired to improve the deviation of the specimens.

A first object of the present invention is to provide a reagent kit, a measurement kit, and a measurement method for measuring serum amyloid A, which enable simple and rapid measurement of serum amyloid A by promoting dissociation of the serum amyloid A from HDL and carrying out an antigen-antibody reaction.

Further, a second object of the present invention is to provide a reagent kit, a measurement kit, and a measurement method for measuring serum amyloid A, which enables a decrease in deviation of a specimen in which large deviation from the control method occurs in the measurement of serum amyloid A.

As a result of intensive examination conducted by the present inventors in order to solve the above-described problems, it was found that the above-described problems can be solved by using first particles having a label and modified with a first binding substance having a property of specifically binding to serum amyloid A, at least one nonionic surfactant having an HLB value of 17 to 20, which is defined by (inorganicity value/organicity value)×10, and having a molecular weight of 1000 or less, and a buffer capable of adjusting the pH of a reaction solution to be in a range of 5.5 to 7.0 or a range of 8.5 to 9.0 in combination, thereby completing the present invention.

That is, according to the present invention, the following inventions are provided.

[1] A reagent kit for measuring serum amyloid A, comprising: first particles having a label and modified with a first binding substance having a property of specifically binding to serum amyloid A; at least one nonionic surfactant having an HLB value of 17 to 20, which is defined by (inorganicity value/organicity value)×10, and a molecular weight of 1000 or less; and a buffer adjusting a pH of a reaction solution to be in a range of 5.5 to 7.0 or a range of 8.5 to 9.0.

[2] The reagent kit according to [1], in which an average particle diameter of the first particles is in a range of 70 nm to 500 nm.

[3] The reagent kit according to [1] or [2], further comprising: second particles which are modified with a second binding substance having no property of specifically binding to serum amyloid A and do not have a label.

[4] The reagent kit according to [3], in which an average particle diameter of the second particles is in a range of 70 nm to 500 nm.

[5] The reagent kit according to any one of [1] to [4], in which the label includes a fluorescent dye.

[6] The reagent kit according to any one of [1] to [5], in which the serum amyloid A is serum amyloid A in cat serum or cat plasma.

[7] The reagent kit according to any one of [1] to [6], in which the buffer is 2-(N-morpholino)ethanesulfonic acid or N,N-bis(2-hydroxyethyl)glycine.

[8] The reagent kit according to any one of [1] to [7], in which the first binding substance is an antibody.

[9] A measurement kit for serum amyloid A, comprising: the reagent kit according to any one of [1] to [8]; and a substrate on which a first metal film on which a third binding substance having a property of specifically binding to serum amyloid A or the first binding substance is fixed is formed.

[10] The measurement kit according to [9], in which a second metal film on which a fourth binding substance which has a property of specifically binding to the first binding substance does not have a property of binding to serum amyloid A is fixed is further formed on the substrate.

[11] A measurement method for serum amyloid A in a biological sample, the method comprising: a step of preparing a mixed solution which contains a biological sample containing serum amyloid A, first particles having a label and modified with a first binding substance having a property of specifically binding to serum amyloid A, at least one nonionic surfactant having an HLB value of 17 to 20, which is defined by (inorganicity value/organicity value)×10, and a molecular weight of 1000 or less, and a buffer adjusting a pH of a reaction solution to be in a range of 5.5 to 7.0 or a range of 8.5 to 9.0; a step of adding the mixed solution to an injection port at one end of a substrate on which a first metal film on which a third binding substance having a property of specifically binding to serum amyloid A is fixed is formed; a step of allowing the mixed solution to flow down onto the substrate; and a step of acquiring information of the label on the first metal film.

[12] The measurement method for serum amyloid A according to [11], in which in a case where the mixed solution is prepared, the biological sample is diluted with physiological saline at a dilution ratio of 4 times to 100 times.

According to the reagent kit, the measurement kit, and the measurement method of the present invention, SAA can be immunologically measured in a simple and rapid manner.

BRIEF DESCRIPTION OF THE DRAWINGS

In FIG. 1 and FIG. 2.

Figure 1:
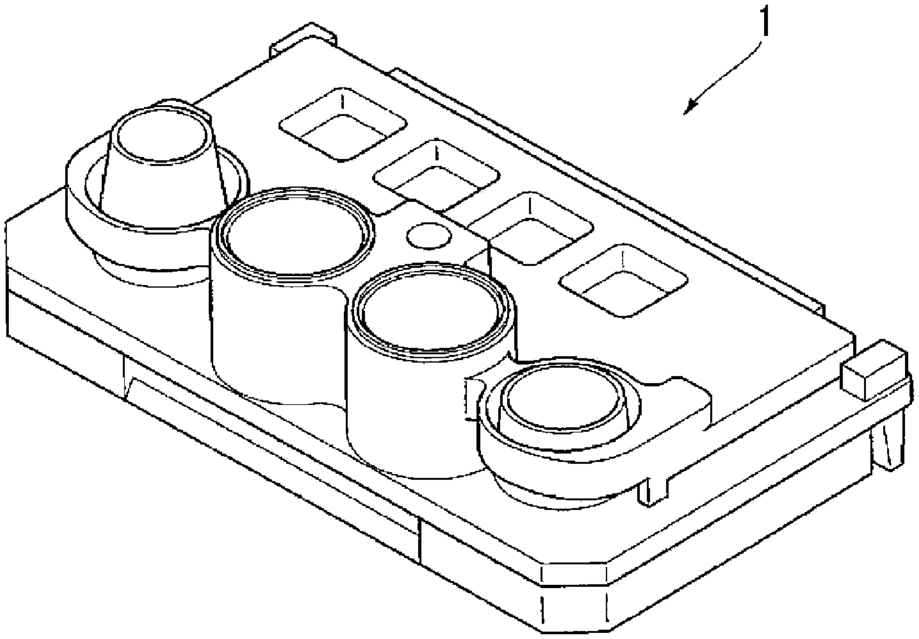
FIG. 1 is a schematic view illustrating a sensor chip.

"1" denotes a measurement kit;

"4" denotes a substrate on which a first metal film is formed, wherein a third binding substance having a property of specifically binding to serum amyloid A or of specifically binding to the first binding substance is fixed to the first metal film. A second metal film may be further formed on the substrate, wherein a fourth binding substance having a property of specifically binding to the first binding substance, but not having a property of binding to serum amyloid A is fixed to the second metal film;

"5" denotes a first container for containing a measurement kit; and

"6" denotes a second container for containing a measurement kit".

DESCRIPTION OF THE PREFERRED EMBODIMENTS

Hereinafter, embodiments of the present invention will be described in detail.

In the present specification, a numerical range shown using "to" indicates a range including the numerical values described before and after "to" as a minimum value and a maximum value, respectively.

[Reagent Kit]

A reagent kit according to the embodiment of the present invention is a reagent kit for measuring serum amyloid A, including first particles having a label and modified with a first binding substance having a property of specifically binding to serum amyloid A, at least one nonionic surfactant having an HLB value of 17 to 20, which is defined by (inorganicity value/organicity value)×10, and a molecular weight of 1000 or less; and a buffer adjusting a pH of a reaction solution to be in a range of 5.5 to 7.0 or a range of 8.5 to 9.0.

The reagent kit according to the embodiment of the present invention includes the first particles, the nonionic surfactant, and the buffer as described above, and the first particles, the nonionic surfactant, and the buffer may be included in the kit separately or in the form of a mixture.

In the present invention, the antigen-antibody reaction is not inhibited even in a case of using a surfactant by blending a surfactant having a specific HLB value at a low concentration, and an SPF signal with a sufficient intensity can be obtained.

(Serum Aamyloid A)

A test substance in the present invention is serum amyloid A (SAA). SAA is useful as an inflammatory marker. Examples of serum amyloid A include serum amyloid A in cat serum or cat plasma.

(Surfactant)

The property of the nonionic surfactant is typically represented by hydrophilic-lipophilic balance (HLB) in the art, and various different methods can be used as the method of calculating the HLB value. In the present invention, it was found that a satisfactory signal intensity is obtained in the SPF measurement system of the present invention by using an organicity value and an inorganicity value based on the organic conceptual diagrams (Organic Conceptual Diagrams—Basics and Applications, new edition, Sankyo Shuppan Co., Ltd., first edition (1984)) and using a nonionic surfactant having an HLB value of 17 to 20, which is defined by (inorganicity value/organicity value)×10 and a molecular weight of 1000 or less.

In the techniques of the related art, it is known to use a surfactant having a preferable HLB value. However, in the present invention, not only the HLB value but also the size of the surfactant molecule are important factors and thus the HLB value and the size thereof are required to be in specific ranges. That is, the condition of the HLB value suitable for dissociating serum amyloid A from HDL is not sufficient because the molecular volume is inevitably increased, the approach of an antibody to serum amyloid A required for the antigen-antibody reaction after dissociation is inhibited, and a decrease in signal particularly in low-concentration specimens is caused in a case where the molecular weight thereof is extremely large. Therefore, it is assumed that the molecular weight is required to be in a certain range so that the surfactant molecule has a specific size.

It is known that most of SAA in serum is present in a state of being associated with high-density lipoprotein (HDL). Therefore, there is a problem in that since a recognition site of serum amyloid A for a first binding substance and a third binding substance having a property of binding to serum amyloid A is shielded by HDL, the first binding substance and the third binding substance are not able to bind to serum amyloid A. According to the present invention, in order to solve such a phenomenon, SAA in serum can be accurately quantified by dissociating serum amyloid A from HDL using a surfactant.

The surfactant used in the present invention is a nonionic surfactant having a molecular weight of 1000 or less. In a case where the molecular weight of the nonionic surfactant is greater than 1000, SAA may not be accurately measured because a site recognized as a specimen similarly to HDL is shielded in some cases. Therefore, a nonionic surfactant having a molecular weight of 1000 or less is used. The lower limit of the molecular weight of the surfactant is preferably 200 or greater and more preferably 300 or greater. The upper limit of the molecular weight of the surfactant is preferably 900 or less, more preferably 800 or less, still more preferably 700 or less, and particularly preferably 600 or less.

In the present invention, a nonionic surfactant that does not relatively affect the binding property of the binding substance is used. An ionic surfactant may affect the measurement by interacting with a charged group in a biological sample, and thus SAA is unlikely to be accurately measured. Accordingly, a nonionic surfactant is used in the present invention. A non-ion-based surfactant may also be noted to as a nonionic surfactant as another name. An anion-based surfactant may also be noted as an anionic surfactant, a cation-based surfactant may also be noted as a cationic surfactant, and an amphoteric surfactant may also be noted as a betaine. In the present invention, a non-ion-based surfactant, that is, a nonionic surfactant is used. As a specific nonionic surfactant, an ether type surfactant is preferable.

As the surfactant, monosaccharides containing a hydrophobic group or disaccharides containing a hydrophobic group are also preferable. As the monosaccharides containing a hydrophobic group or the disaccharides containing a hydrophobic group, a compound having a glucose skeleton or a maltose skeleton is more preferable. Examples of the compound having a glucose skeleton or a maltose skeleton include a compound represented by Formula (2) or Formula (3).

(2)

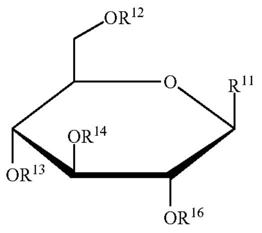

(3)

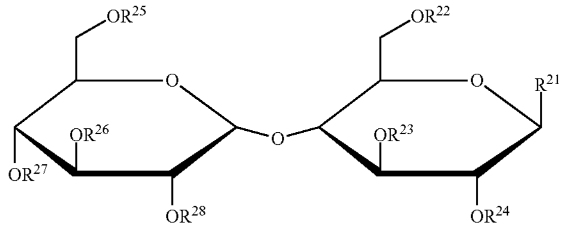

In the formula, $R^{11}$ represents an alkoxy group which may be substituted, an alkenyloxy group which may be substituted, an alkynyloxy group which may be substituted, an alkylthio group which may be substituted, an alkenylthio group which may be substituted, or an alkynylthio group which may be substituted, and $R^{12}$, $R^{13}$, $R^{14}$, and $R^{15}$ each independently represent a hydrogen atom or a hydrocarbon group which may be substituted. Here, at least three of $R^{12}$, $R^{13}$, $R^{14}$, and $R^{15}$ are hydrogen atoms.

In the formula, $R^{21}$ represents an alkoxy group which may be substituted, an alkenyloxy group which may be substituted, an alkynyloxy group which may be substituted, an alkylthio group which may be substituted, an alkenylthio group which may be substituted, or an alkynylthio group which may be substituted, and $R^{22}$, $R^{23}$, $R^{24}$, $R^{25}$, $R^{26}$, $R^{27}$, and $R^{28}$ each independently represent a hydrogen atom or a hydrocarbon group which may be substituted. Here, at least three of $R^{22}$, $R^{23}$, $R^{24}$, $R^{25}$, $R^{26}$, $R^{27}$, and $R^{28}$ are hydrogen atoms. More preferred examples of the compound represented by Formula (2) or Formula (3) include a compound represented by Formula (2A) or Formula (3A).

(2A)

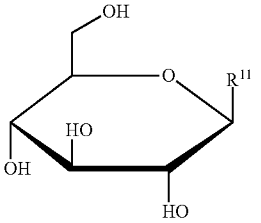

(3A)

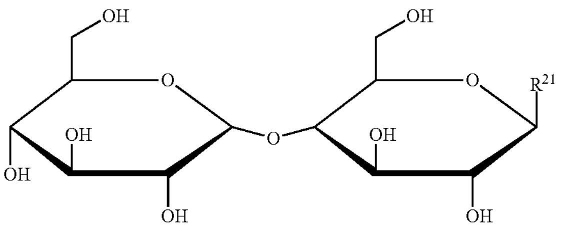

In the formula, $R^{11}$ and $R^{21}$ each have the same definition as in Formulae (2) and (3).

As the compound represented by Formula (2A), it is preferable to use the following surfactants.

n-Octyl-β-D-glucoside (0001, manufactured by Dojindo Co., Ltd.) A compound in which $R^{11}$ in Formula (2A) represents an octyloxy group.

As the compound represented by Formula (3A), it is preferable to use the following surfactants.

n-Dodecyl-β-D-maltoside (D316, manufactured by Dojindo Co., Ltd.)

n-Decyl-β-D-maltoside (D382, manufactured by Dojindo Co., Ltd.)

The hydrocarbon group, the alkoxy group, the alkenyloxy group, the alkynyloxy group, the alkylthio group, the alkenylthio group, and the alkynylthio group may be substituted, and examples of the substituents include substituents described in the following substituent group A. The substituents of the substituent group A may be further substituted with the substituents of the substituent group A.

The substituent group A includes: a sulfamoyl group, a cyano group, an isocyano group, a thiocyanato group, an isothiocyanato group, a nitro group, a nitrosyl group, a halogen atom, a hydroxy group, an amino group, a mercapto group, an amide group, an alkoxy group, an aryloxy group, an alkylthio group, an arylthio group, a carbamoyl group, an acyl group, an aldehyde group, a carbonyl group, an aryl group, an alkyl group, an alkyl group substituted with a halogen atom, an ethenyl group, an ethynyl group, a silyl group, and a trialkylsilyl group (a trimethylsilyl group or the like).

Examples of the hydrocarbon group may include an alkyl group, an alkenyl group, and an alkynyl group. The number of the carbon atoms of the hydrocarbon group is not particularly limited, but is typically in a range of 1 to 20, preferably in a range of 1 to 16, and more preferably in a range of 1 to 12.

The number of carbon atoms of the alkoxy group, the alkenyloxy group, the alkynyloxy group, the alkylthio group, the alkenylthio group, or the alkynylthio group is not particularly limited, but is typically in a range of 1 to 20, preferably in a range of 1 to 16, and more preferably in a range of 1 to 12.

(Buffer (Buffer Solution))

In the present invention, a buffer capable of adjusting the pH of a reaction solution to be in a range of 5.5 to 7.0 or a range of 8.5 to 9.0 is used in order to improve deviation of specimens in which deviation is not improved only with the following second particles of the present invention, among deviation specimens. The deviation between the measurement values of the present invention from the values acquired by the control method is considered to be caused by various foreign substances in the antigen-antibody reaction, and the mechanism thereof also varies. Therefore, for example, the present object is achieved by adjusting the pH of the reaction solution such that the antigen-antibody reaction is not affected based on the consideration that the reactivity with the foreign substances is changed due to the pH of the reaction solution.

As the buffer used in the present invention, a good buffer is preferable, and a buffer capable of adjusting the pH of the reaction solution to be in a range of 5.5 to 7.0 or a range of 8.5 to 9.0 is preferably used. Preferred examples of the buffer capable of adjusting the pH of the reaction solution to be in a range of 5.5 to 7.0 include MES (2-(N-morpholino) ethanesulfonic acid), ADA (N-(2-acetamide)iminodiacetic acid), PIPES (piperazine-1,4-bis(2-ethanesulfonic acid) sesquisodium salt monohydrate), ACES (N-(2-acetamide)-2-aminoethanesulfonic acid), Bis-Tris (bis(2-hydroxyethyl) iminotris(hydroxymethyl)methane), MOPSO (2-hydroxy-3-morpholinopropanesulfonic acid), BES (N,N-bis(2-hydroxyethyl)-2-aminoethanesulfonic acid), MOPS (3-morpholinopropanesulfonic acid), TES (N-tris(hydroxymethyl)methyl-2-aminoethanesulfonic acid), and HEPES (2-[4-(2-hydroxyethyl)-1-piperazinyl]ethanesulfonic acid).

Among these, MES can be particularly preferably used.

Preferred examples of the buffer capable of adjusting the pH of the reaction solution to be in a range of 8.5 to 9.0 include POPSO (piperazine-1,4-bis(2-hydroxy-3-propanesulfonic acid) dihydrate), HEPPSO (2-hydroxy-3-[4-(2-hydroxyethyl)-1-piperazinyl]propanesulfonic acid) monohydrate), EPPS (3-[4-(2-hydroxyethyl)-1-piperazinyl] propanesulfonic acid), Tricine (N-[tris(hydroxymethyl) methyl]glycine), Bicine (N,N-bis(2-hydroxyethyl)glycine), TAPS (N-tris(hydroxymethyl)methyl-3-aminopropanesulfonic acid), and CHES (N-cyclohexyl-2-aminoethanesulfonic acid).

Among these, Bicine can be particularly preferably used.

(First Binding Substance)

The first binding substance used in the present invention is a substance having a property of specifically binding to serum amyloid A. An antibody can be used as the first binding substance, but the present invention is not limited thereto. It is preferable that the first binding substance is an antibody. In a case where the first binding substance is an antibody, as an antibody having a property of specifically binding to serum amyloid A, for example, antiserum prepared from serum of an animal immunized with serum amyloid A, an immunoglobulin fraction purified from antiserum, a monoclonal antibody obtained by cell fusion using spleen cells of an animal immunized with serum amyloid A, or fragments thereof [for example, $F(ab')_2$, Fab, Fab', or Fv] can be used. These antibodies can be prepared by a method of the related art. Further, the antibody may be modified as in a case where the antibody is a chimeric antibody or the like. In addition, a commercially available antibody or an antibody prepared from animal serum or culture supernatant according to a known method can also be used.

The antibody can be used regardless of the animal species or subclass. For example, antibodies that can be used in the present invention are antibodies derived from organisms, in which an immune reaction can occur, such as a mouse, a rat, a hamster, a goat, a rabbit, a sheep, a bovine, and a chicken, and specific examples thereof include mouse IgG, mouse IgM, rat IgG, rat IgM, hamster IgG, hamster IgM, rabbit IgG, rabbit IgM, goat IgG, goat IgM, sheep IgG, sheep IgM, bovine IgG, bovine IgM, and chicken IgY. Further, either of polyclonal or monoclonal can be used.

In particular, an antiserum amyloid A antibody is preferably used as the first binding substance having a property of specifically binding to serum amyloid A due to electrostatic interaction. In the present invention, it is preferable to select a sandwich method. In this case, it is necessary to coat the substrate with a pair of antibodies, but these anti-SAA monoclonal antibodies can be used on both the substrate and the first particle.

(First Particle)

The first particles used in the present invention are particles having a label and modified with the above-described first binding substance.

It is preferable that the first particles are dry particles, but the present invention is not particularly limited. As the first particles, for example, polymer particles such as polystyrene beads and glass particles such as glass beads can be used as particles which can be typically used for immunoassay. Specific examples of the material of the first particles include polymers formed of a monomer such as styrene, methacrylic acid, glycidyl (meth)acrylate, butadiene, vinyl chloride, vinyl acetate acrylate, methyl methacrylate, ethyl methacrylate, phenyl methacrylate, or butyl methacrylate; and synthetic polymers such as copolymers formed of two or more monomers. A latex obtained by uniformly suspending these polymers is preferable. Further, other examples thereof include organic polymer powder, inorganic substance powder, microorganisms, blood cells, cell membrane pieces, and liposomes.

In a case of using latex particles, specific examples of the material of the latex include polystyrene, a styrene-acrylic acid copolymer, a styrene-methacrylic acid copolymer, a styrene-glycidyl (meth)acrylate copolymer, a styrene-styrene sulfonate copolymer, a methacrylic acid polymer, an acrylic acid polymer, an acrylonitrile-butadiene-styrene copolymer, a vinyl chloride-acrylic acid ester copolymer, and polyvinyl acetate acrylate. As the latex, a copolymer containing at least styrene as a monomer is preferable, and a copolymer of styrene and acrylic acid or methacrylic acid is particularly preferable. The method for preparing the latex is not particularly limited, and can be prepared according to an optional polymerization method. Here, since antibody immobilization is unlikely to be carried out in a case where a surfactant is present during antibody labeling, emulsifier-free emulsion polymerization, that is, emulsion polymerization that does not use an emulsifier such as a surfactant is preferable for preparing the latex.

The first particles have a label. It is preferable that the label emits fluorescence. In a case where the latex obtained by polymerization is fluorescent, the latex can be directly used as fluorescent latex particles. In a case where the latex obtained by polymerization is non-fluorescent, fluorescent latex particles can be prepared by adding a fluorescent substance (such as a fluorescent dye) to the latex. That is, the fluorescent latex particles can be produced by adding a fluorescent dye to a latex particle solution containing water and a water-soluble organic solvent and stirring the solution or impregnating latex particles with a fluorescent dye.

As the first particles having a label, liposomes or microcapsules containing a fluorescent dye can also be used as fluorescent particles. The fluorescent color is not particularly limited as long as the color is emitted in a case of absorption of ultraviolet light or the like for excitation and returning to the ground state. For example, fluorescent colors such as yellow-green (excitation wavelength of 505 nm/emission wavelength of 515 nm, the same applies hereinafter), blue (350 to 356 nm/415 to 440 nm), red (535 to 580 nm/575 to 605 nm), orange (540 nm/560 nm), red orange (565 nm/580 nm), crimson (625 nm/645 nm), and dark red (660 nm/680 nm) can be used. These fluorescent particles emitting fluorescence are available from, for example, Invitrogen and are commercially available under the trade name of FluoSpheres (registered trademark) manufactured by the same company.

The particle diameter of the first particles having a label is defined as the average particle diameter. The average particle diameter of the first particles is not particularly limited, and the preferable range thereof varies depending on the material of the particles, the concentration range where serum amyloid A is quantified, the measuring instrument, and the like. Further, the average particle diameter thereof is preferably in a range of 70 nm to 500 nm, more preferably in a range of 70 nm to 300 nm, still more preferably in a range of 80 nm to 250 nm, and particularly preferably in a range of 90 nm to 200 nm.

The average particle diameter of the particles used in the present invention can be measured with a commercially available particle size distribution meter or the like. As the method of measuring the particle size distribution, an optical microscopy method, a confocal laser microscopy method, an electron microscopy method, an atomic force microscopy method, a static light scattering method, a laser diffraction method, a dynamic light scattering method, a centrifugal sedimentation method, an electric pulse measurement method, a chromatography method, an ultrasonic attenuation method, and the like are known, and devices corresponding to each principle are commercially available. Among these measurement methods, it is preferable that the particle size distribution is measured using a dynamic light scattering method. In the present invention, the average particle diameter is acquired as a median diameter (50% diameter, d50) measured under conditions of a viscosity of 0.8872 CP (0.8872 mPa·s) and a water refractive index of 1.330 at 25° C.

The first particles used in the present invention are modified with the above-mentioned first binding substance. The method for binding the first binding substance to the first particles having a label is not particularly limited. For example, the method is described in JP2000-206115A and the protocol attached to FluoSpheres (registered trademark) polystyrene microsphere F8813 (manufactured by Molecular Probes Inc.), and any known method of preparing a reagent for an immunoaggregation reaction can be used. Further, as a method of immobilizing a binding substance such as an antibody on a particle, any of a method using physical adsorption and a method using a chemical bond with a covalent bond can be employed. As a blocking agent covering the surface of a particle that is not coated with a binding substance after the binding substance such as an antibody is fixed to the particle, known substances such as BSA (bovine serum albumin), skim milk, casein, soybean-derived components, fish-derived components, and polyethylene glycol; and commercially available blocking agents for an immune reaction which contain these substances or substances having the same properties as those of these substances can be used. These blocking agents can be subjected to a pretreatment such as partial denaturation with heat, an acid, an alkali, or the like as necessary.

(Second Binding Substance)

The reagent kit according to the embodiment of the present invention may further include second particles which are modified with a second binding substance with no property of specifically binding to serum amyloid A, but do not have a label.

A test sample which is positive after reaction with not only a positive test sample containing serum amyloid A but also a negative test sample containing no serum amyloid A exists, and resolving of false positives is recognized as a task. Although the reason for showing such a false positive has not been clarified, one reason is considered to be that the presence of some factor contained in serum causes a non-specific reaction. In the present invention, it is preferable to solve such a problem by using second particles, which are modified with a second binding substance with no property of specifically binding to serum amyloid A, but do not have a label, in combination.

As the second binding substance, a substance that does not have a property of specifically binding to serum amyloid A can be used, a substance that may bind to a causative substance showing such a false positive as described above is preferably used, and a compound with no affinity for the first binding substance is more preferably used. As the second binding substance, an antibody, a protein (Protein A or Protein G) that binds to an antibody, or the like can be used, and an antibody is preferable. For example, in a case where the second binding substance is an antibody, antiserum prepared from serum of an animal immunized with an antigen thereof, an immunoglobulin fraction purified from antiserum, a monoclonal antibody obtained by cell fusion using spleen cells of an animal immunized with serum amyloid A, or fragments thereof [for example, $F(ab')_2$, Fab, Fab', or Fv] can be used. These antibodies can be prepared by a method of the related art. Further, the antibody may be modified as in a case where the antibody is a chimeric antibody or the like. In addition, a commercially available antibody or an antibody prepared from animal serum or culture supernatant according to a known method can also be used. In the present invention, a substance using an anti-CRP antibody is preferable as the second binding substance.

(Second Particle)

The second particles do not have a label. Further, it is preferable that the second particles are dry particles, but the present invention is not particularly limited thereto.

As the second particles, for example, polymer particles such as polystyrene beads and glass particles such as glass beads can be used as particles that can be typically used for immunoassay. Specific examples of the material of the second particles include polymers formed of a monomer such as styrene, methacrylic acid, glycidyl (meth)acrylate, butadiene, vinyl chloride, vinyl acetate acrylate, methyl methacrylate, ethyl methacrylate, phenyl methacrylate, or butyl methacrylate; and synthetic polymers such as copolymers formed of two or more monomers, and a latex obtained by uniformly suspending these polymers is preferable. Further, other examples thereof include organic polymer powder, inorganic substance powder, microorganisms, blood cells, cell membrane pieces, and liposomes.

In a case of using latex particles, specific examples of the material of the latex include polystyrene, a styrene-acrylic acid copolymer, a styrene-methacrylic acid copolymer, a styrene-glycidyl (meth)acrylate copolymer, a styrene-styrene sulfonate copolymer, a methacrylic acid polymer, an acrylic acid polymer, an acrylonitrile-butadiene-styrene copolymer, a vinyl chloride-acrylic acid ester copolymer, and polyvinyl acetate acrylate. As the latex, a copolymer containing at least styrene as a monomer is preferable, and a copolymer of styrene and acrylic acid or methacrylic acid is particularly preferable. The method for preparing the latex is not particularly limited, and can be prepared according to an optional polymerization method. Here, since antibody immobilization is unlikely to be carried out in a case where a surfactant is present during antibody labeling, emulsifier-free emulsion polymerization, that is, emulsion polymerization that does not use an emulsifier such as a surfactant is preferable for preparing the latex.

The particle diameter of the second particles bound with the second binding substance is defined as the average particle diameter. The average particle diameter of the second particles varies depending on the material of the particles, the concentration range where serum amyloid A is quantified, the measuring instrument, and the like, and the average particle diameter thereof is preferably in a range of 70 nm to 500 nm, more preferably in a range of 100 nm to 200 nm, still more preferably in a range of 120 nm to 180 nm, and particularly preferably in a range of 130 nm to 170 nm.

In regarding to the use ratio between the first particles and the second particles, the mass ratio of the second particles to the first particles is preferably in a range of 1 to 10, more preferably in a range of 1 to 6, and still more preferably in a range of 2 to 6.

[Measurement Kit]

A measurement kit according to the embodiment of the present invention includes the above-described reagent kit according to the embodiment of the present invention, and a substrate on which a first metal film on which a third binding substance (that is, a third binding substance having a property of specifically binding to serum amyloid A or a third binding substance having a property of specifically binding to the first binding substance) having a property of specifically binding to serum amyloid A or the first binding substance is fixed is formed. A second metal film on which a fourth binding substance which has a property of specifically binding to the first binding substance but does not have a property of binding to serum amyloid A is fixed may be further formed on the substrate.

(Third Binding Substance)

The third binding substance is not particularly limited as long as the third binding substance is a substance having a property of specifically binding to serum amyloid A or the first binding substance, and preferred examples thereof include an antigen, an antibody, and a complex thereof. Among these, it is more preferable to use an antibody. In a case where the third binding substance is an antibody, as an antibody having a specificity for serum amyloid A, for example, antiserum prepared from serum of an animal immunized with serum amyloid A, an immunoglobulin fraction purified from antiserum, a monoclonal antibody obtained by cell fusion using spleen cells of an animal immunized with serum amyloid A, or fragments thereof [for example, $F(ab')_2$, Fab, Fab', or Fv] can be used. These antibodies can be prepared by a method of the related art. Further, the antibody may be modified as in a case where the antibody is a chimeric antibody or the like. In addition, a commercially available antibody or an antibody prepared from animal serum or culture supernatant according to a known method can also be used.

The antibody can be used regardless of the animal species or subclass. For example, antibodies that can be used in the present invention are antibodies derived from organisms, in which an immune reaction can occur, such as a mouse, a rat, a hamster, a goat, a rabbit, a sheep, a bovine, and a chicken, and specific examples thereof include mouse IgG, mouse IgM, rat IgG, rat IgM, hamster IgG, hamster IgM, rabbit IgG, rabbit IgM, goat IgG, goat IgM, sheep IgG, sheep IgM, bovine IgG, bovine IgM, and chicken IgY. Further, either of polyclonal or monoclonal can be used. Fragmented antibodies are molecules having at least one antigen-binding site and derived from a complete antibody, and specific examples thereof include Fab and $F(ab')_2$ or the like. These fragmented antibodies are molecules obtained by using enzymes, performing chemical treatments, or using genetic engineering methods.

The third binding substance having a property of specifically binding to the first binding substance is not particularly limited, but preferred examples thereof include an antigen, an antibody, and a complex thereof. The method of preparing an antibody and the kind of the antibody are the same as those described above.

(Fourth Binding Substance)

The fourth binding substance is a substance which has a property of specifically binding to the first binding substance, but does not have a property of binding to serum amyloid A. As the fourth binding substance, it is preferable to use a compound having an affinity for the first binding substance, for example, an antibody that binds to the first binding substance (antibody), a protein (Protein A or Protein G) that binds to a binding substance (antibody), or the like. Among these, it is more preferable to use an antibody. The method of preparing an antibody and the kind of the antibody are the same as those for the third binding substance. Further, a compound in which a part of the first binding substance binding to the first particles having a label and the fourth binding substance are in a ligand-non-ligand relationship can be preferably used.

(Method of Immobilizing Binding Substance on Substrate)

A method of immobilizing the third binding substance and the fourth binding substance such as antibodies on a substrate is described in, for example, Tech Notes Vol. 2-12 provided by Nunc, and any known method of preparing a typical enzyme-linked immunosorbent assay (ELISA) reagent can also be used. Further, surface modification may be carried out by disposing a self-assembled monolayer (SAM) or the like on the substrate. Further, as a method for immobilizing the antibody as a binding substance on the substrate, any of a method using physical adsorption and a method using a chemical bond with a covalent bond can be employed. As a blocking agent covering the surface of a substrate that is not coated with an antibody after the antibody is fixed to the substrate, known substances such as BSA (bovine serum albumin), skim milk, casein, soybean-derived components, fish-derived components, and polyethylene glycol; and commercially available blocking agents for an immune reaction which contain these substances or substances having the same properties as those of these substances can be used. These blocking agents can be subjected to a pretreatment such as partial denaturation with heat, an acid, an alkali, or the like as necessary.

(Substrate)

The substrate used in the present invention is a substrate on which a metal film is formed, and the form thereof is not particularly limited. However, in a case of performing a fluorescence detection method (SPF method) by surface plasmon excitation described below, it is preferable to use a substrate including a flow path described below and a metal film which is a reaction site on the surface. As the metal constituting the metal film, a substance that can cause surface plasmon resonance can be used. Preferred examples of the metal include metals such as gold, silver, copper, aluminum, and platinum. Among these, gold is particularly preferable. The above-described metals can be used alone or in combination. Further, in consideration of the adhesiveness to the substrate, an intervening layer consisting of chromium and the like may be provided between the substrate and the layer consisting of metals. The film thickness of the metal film is not particularly limited, but is preferably in a range of 0.1 nm to 500 nm, more preferably in a range of 1 nm to 200 nm, and particularly preferably in a range of 1 nm to 100 nm. In a case where the film thickness is greater than 500 nm, the surface plasmon phenomenon of the medium cannot be sufficiently detected. Further, in a case where an intervening layer consisting of chromium and the like is provided, the thickness of the intervening layer is preferably in a range of 0.1 nm to 10 nm.

The metal film may be formed by a method of the related art. For example, the metal film can be formed by a sputtering method, a magnetron sputtering method, a vapor deposition method, an ion plating method, an electrolytic plating method, an electroless plating method, or the like, but it is preferable that the metal film is formed by a sputtering method in order to realize satisfactory adhesiveness of the metal film to the substrate.

It is preferable that the metal film is disposed on the substrate. Here, the expression of "disposed on the substrate" includes a case where the metal film is disposed so as to be in direct contact with the substrate and a case where the metal film is disposed on the substrate through another layer without being in direct contact with the substrate. Examples of the substrate that can be used in the present invention include optical glass such as BK7 (borosilicate glass) which is a kind of typical optical glass; and synthetic resins, specifically, those consisting of materials transparent to laser light, such as polymethyl methacrylate, polyethylene terephthalate, polycarbonate, and a cycloolefin polymer. As the material of such a substrate, preferably, a material that does not exhibit anisotropy with respect to polarized light and has excellent workability is desirable. As an example of the substrate for detecting fluorescence by the SPF method, a substrate in which a gold film is prepared on polymethyl methacrylate by a sputtering method can be exemplified.

[Measurement Method for Serum Amyloid A]

The measurement method for serum amyloid A in a biological sample according to the embodiment of the present invention includes a step of preparing a mixed solution which contains a biological sample containing serum amyloid A, first particles having a label and modified with the first binding substance having a property of specifically binding to serum amyloid A, at least one nonionic surfactant having an HLB value of 17 to 20, which is defined by (inorganicity value/organicity value)×10, and a molecular weight of 1000 or less, and a buffer adjusting a pH of a reaction solution to be in a range of 5.5 to 7.0 or a range of 8.5 to 9.0; a step of adding the mixed solution to an injection port at one end of a substrate on which a first metal film on which a third binding substance having a property of specifically binding to serum amyloid A is fixed is formed; a step of allowing the mixed solution to flow down onto the substrate; and a step of acquiring information of the label on the first metal film.

The biological sample is not particularly limited as long as the sample possibly contains serum amyloid A which is a test substance, and examples thereof include biological samples, particularly body fluids (such as blood, serum, plasma, cerebrospinal fluid, lacrimal fluid, sweat, urine, pus, nasal mucus, and sputum) of animals (particularly cats, dogs, and humans), excrements (such as feces), organs, tissues, mucous membranes, and skin.

A nonionic surfactant is used for a pretreatment applied to a biological sample containing SAA. A pretreatment liquid is used according to a use method of preparing a liquid containing a surfactant in advance and mixing the prepared liquid with a specimen liquid or a use method of adding a surfactant of a dried solid content to a biological sample liquid and dissolving the surfactant in a specimen liquid. In this case, the concentration of the surfactant in the mixed solution obtained by mixing the biological sample liquid with the surfactant is preferably in a range of 0.01% by mass to 10% by mass, more preferably in a range of 0.05% by mass to 5% by mass, still more preferably in a range of 0.1% by mass to 3% by mass, and particularly preferably in a range of 0.1% by mass to 2% by mass. In a case where the concentration thereof is 0.01% by mass or greater, SAA can be effectively separated from HDL. Further, in a case where the concentration thereof is 10% by mass or less, the first binding substance on the first particles having a label or the second binding substance fixed to the first metal film on the substrate can react with SAA in a state where the reaction is unlikely to be affected by the surfactant.

The mixed solution may further contain second particles modified with the second binding substance which does not have a property of specifically binding to serum amyloid A.

Further, the measurement method for serum amyloid A according to the embodiment of the present invention may further include a step of bringing the mixed solution into contact with a second metal film on which a fourth binding substance which has a property of binding to the first binding substance but does not have a property of binding to serum amyloid A is fixed; a step of detecting a signal from the second metal film corresponding the label; and a step of correcting a signal detected from the first metal film using the signal detected from the second metal film.

(Measurement Method)

The measurement method according to the embodiment of the present invention is interpreted as the broadest concept including detection of the presence or absence of serum amyloid A, measurement (that is, quantification) of the amount of serum amyloid A, and the like. Specific examples of the measurement method according to the embodiment of the present invention include a sandwich method and a competitive method. Among these, the sandwich method is preferable.

<Sandwich Method>

The sandwich method is not particularly limited, but serum amyloid A can be measured, for example, by the following procedures. First, a first binding substance having a property of specifically binding to serum amyloid A and a third binding substance having a property of specifically binding to serum amyloid A are prepared in advance. The first binding substance is bound to the first particles having a label to prepare the first particles modified with the first binding substance having a property of specifically binding to serum amyloid A. Next, a third binding substance is prepared and fixed onto the substrate to form a reaction site (test area). Further, a fourth binding substance is prepared and fixed onto the substrate to form a control area. Separately, a second binding substance which does not have a property of specifically binding to serum amyloid A is prepared and bound to the second particles having no label so that the second particles having no label and modified with the second binding substance which does not have a property of specifically binding to serum amyloid A are prepared. The above-described first particles and second particles are mixed, stored in a container, and dried. A test sample (or an extracted liquid thereof) that may contain serum amyloid A, a mixture of the first particles and the second particles, and a surfactant are mixed, and the mixed solution is applied to a substrate and allowed to spread on a flow path on the substrate so as to come into contact with the reaction site. In a case where serum amyloid A is present in the test sample, the reaction (the antigen-antibody reaction in a case of using an antigen and an antibody) occurs between the serum amyloid A and the first binding substance bound to the first particles on the reaction site and between the serum amyloid A and the third binding substance on the reaction site, and the first particles according to the amount of serum amyloid A are fixed onto the reaction site. According to the sandwich method, after the reaction between the third binding substance fixed onto the reaction site and serum amyloid A and the reaction between serum amyloid A and the first binding substance bound to the first particles are completed, washing can also be performed for the purpose of removing the first particles that have not been bound to the test area and the control area on the substrate. Next, the concentration of serum amyloid A can be accurately measured by detecting the signal intensity from the first particles bound to the reaction site. Further, the fluorescence intensity and the concentration of serum amyloid A have a positive correlation.

<Competitive Method>

The competitive method is not particularly limited, but serum amyloid A can be measured, for example, by the following procedures. The competitive method is well known in the art as a method of detecting an antigen of a low-molecular-weight compound that cannot be assayed by the sandwich method. First, a first binding substance having a property of specifically binding to serum amyloid A and a second binding substance which does not have a property of specifically binding to serum amyloid A are prepared in advance. Next, the first binding substance is bound to the first particles, and the second binding substance is bound to the second particles. Further, serum amyloid A which has a property of binding to the first binding substance or a compound having a site similar to serum amyloid A and having an epitope for the first binding substance which is the same as serum amyloid A is fixed onto the substrate to form a reaction site. Next, the first particles and the second particles are mixed, stored in a container, and dried. A test sample (or an extracted liquid thereof) that may contain serum amyloid A, a mixture of the first particles and the second particles, and a surfactant are mixed, and the mixed solution is allowed to spread on a flow path on the substrate so as to come into contact with the reaction site. In a case where serum amyloid A is not present in the test sample, the reaction occurs on the substrate due to the first binding substance bound to the first particles and a similar compound having an epitope for serum amyloid A having a property of binding to the first binding substance fixed onto the reaction site or a first binding substance antibody similar to serum amyloid A. Meanwhile, in a case where serum amyloid A is present, since serum amyloid A is bound to the first binding substance, the reaction, on the reaction site, between serum amyloid A having a property of binding to the first binding substance or a compound having a site similar to serum amyloid A and having an epitope for the first binding substance antibody which is the same as serum amyloid A is inhibited, and fixing of the first particles having a label onto the reaction site is inhibited. According to the competitive method, a plurality of samples with different concentrations of serum amyloid A and known amounts of serum amyloid are prepared in advance, fluorescence signals from the reaction sites are measured at a plurality of different times while the samples and binding material-labeled fluorescent particles are brought into contact with each other on the reaction sites. Based on the plurality of measurement results, a change (inclination) in time of the fluorescence amount at each concentration of serum amyloid A. The change in time is plotted on a Y-axis and the concentration of serum amyloid A is plotted on an X-axis, and a calibration curve of the concentration of serum amyloid A with respect to the change in time of the fluorescence amount is obtained using a suitable fitting method such as the least squares method as appropriate. Based on the calibration curve obtained in the above-described manner, the amount of serum amyloid A contained in the test sample can be quantified from the result of the change in time of the fluorescence amount using the target test sample.

(Flow Path)

According to a preferred embodiment of the present invention, a mixture is prepared by mixing a test sample (or an extracted liquid thereof) that may contain serum amyloid A, first particles having a label, a surfactant, and a second particle as desired. The mixture can be applied onto the substrate and allowed to spread on the flow path. The flow path is not particularly limited as long as the flow path is a passage that allows the test sample and the first particles (and the second particle as desired) having a label flow down onto the reaction site. According to a preferred embodiment of the flow path, a spotting port that spots a test sample solution containing the first particles (and the second particles as desired) having a label, a metal thin film as a reaction site on which the third binding substance is immobilized, and a flow path beyond the metal thin film exist, and the structure thereof is formed such that the test sample can pass over the metal thin film. It is preferable that a suction port is provided on a side of the metal thin film opposite to the spotting port.

(Method of Detecting Signal Corresponding to Label)

In the present invention, a signal corresponding to the label is detected. As described above, it is preferable that the label emits fluorescence. In this case, a signal corresponding to the label can be detected by detecting the fluorescence. As a method of detecting fluorescence, it is preferable that the fluorescence intensity is detected using, for example, a device capable of detecting the fluorescence intensity, specifically, a microplate reader, or a biosensor for performing a fluorescence detection method (SPF method) by surface plasmon excitation. The detection of the fluorescence intensity is completed typically after a certain time, for example, several minutes to several hours from the antigen-antibody reaction. The concentration of serum amyloid A can be quantified from the relationship between the fluorescence intensity and the concentration of serum amyloid A by detecting the degree of formation of an immune complex as the fluorescence intensity. Further, the fluorescence may be measured in the form of plate reader measurement or flow measurement. In addition, the SPF method enables measurement with higher sensitivity than that of the fluorescence detection method carried out using epi-illumination excitation (epi-fluorescence method).

As a surface plasmon fluorescence (SPF) biosensor, for example, a sensor comprising an optical waveguide formed of a material that transmits excitation light having a predetermined wavelength as described in JP2008-249361A; a metal film formed on one surface of the optical waveguide; a light source that generates light beams; an optical system that allows the light beams to pass through the optical waveguide and to be incident on the interface between the optical waveguide and the metal film at an incidence angle at which a surface plasmons is generated; and a fluorescence detecting unit that detects fluorescence generated by being excited due to evanescent waves enhanced by the surface plasmon can be used.

(Method of Measuring Amount of Serum Amyloid A)

As an example of the method of quantifying serum amyloid A by the SPF method of the present invention, serum amyloid A can be quantified by the following method. Specifically, samples containing serum amyloid A with known concentrations are prepared, and fluorescence signals from the fluorescence detection sites are measured at a plurality of different times while the sites for detecting the fluorescence are allowed to flow down. Based on the plurality of measurement results, a change (inclination) in time of the fluorescence amount at each concentration of serum amyloid A. The change in time is plotted on a Y-axis and the concentration of serum amyloid A is plotted on an X-axis, and a calibration curve of the concentration of serum amyloid A with respect to the change in time of the fluorescence amount is obtained using a suitable fitting method such as the least squares method as appropriate. As the optical signal system, the amount of serum amyloid A in a target test sample can be specified based on the calibration curve corresponding to each serum amyloid A.

The fluorescence detection (SPF) system using surface plasmon excitation in the present invention is an assay method of detecting fluorescence from a fluorescent substance depending on the amount of serum amyloid A immobilized on a metal thin film on a substrate, which is a method different from a so-called latex aggregation method in which a change in optical transparency is detected as, for example, turbidity based on the progress of the reaction in a solution. According to the latex aggregation method, an antibody-sensitized latex in a latex reagent and an antigen in a specimen are bound due to the antibody reaction and aggregated. The aggregate increases with time, and a method of quantifying the antigen concentration from a change in absorbance per unit time obtained by irradiating the aggregate with near infrared light is a latex aggregation method. In the present invention, a method of detecting serum amyloid A which is extremely simple as compared with the latex aggregation method can be provided.

Hereinafter, the present invention will be described in more detail with reference to examples of the present invention. Further, the materials, the use amounts, the ratios, the treatment contents, the treatment procedures, and the like shown in the following examples can be appropriately changed without departing from the spirit of the present invention. Therefore, the scope of the present invention should not be limitatively interpreted by the specific examples described below. In the chemical formulae shown below, Et represents ethyl.

EXAMPLES

The following surfactants were used.

D316: n-dodecyl-β-D-maltoside (manufactured by Dojindo Co., Ltd.), a compound in which R in Formula (A) represents a dodecyloxy group D382: n-decyl-β-D-maltoside (manufactured by Dojindo Co., Ltd.), a compound in which R in Formula (A) represents a decyloxy group (A)

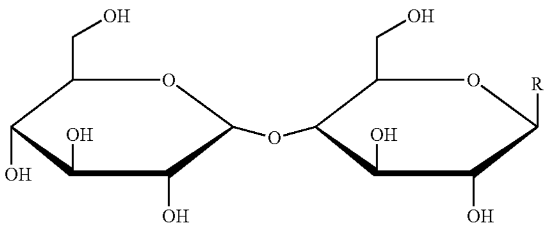

O393: n-octyl-β-D-maltoside (manufactured by Dojindo Co., Ltd.)

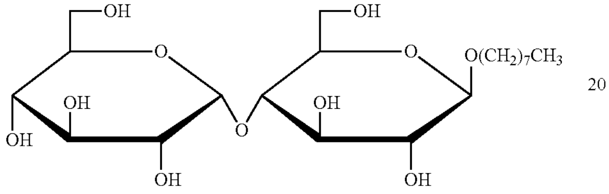

Laureth 10: POE (10) lauryl ether (EMALEX (registered trademark) 710 manufactured by Nippon Emulsion Co., Ltd.)

Laureth 20: POE (20) lauryl ether (EMALEX (registered trademark) 720 manufactured by Nippon Emulsion Co., Ltd.)

Laureth 30: POE (30) lauryl ether (EMALEX (registered trademark) 730 manufactured by Nippon Emulsion Co., Ltd.)

Polyglyceryl-5 laurate: glycerin 5-12 alkyl ester (SUNSOFT A-12E-C, manufactured by Taiyo Kagaku Co., Ltd.)

Polyglyceryl-5 myristate: glycerin 5-14 alkyl ester (SUNSOFT A-14E-C, manufactured by Taiyo Kagaku Co., Ltd.)

Polyglyceryl-6 caprylate: glycerin 6-8 alkyl ester (SUNSOFT Q-81F-C, manufactured by Taiyo Kagaku Co., Ltd.)

Example 1

(1) Production of Latex Particles Having Average Particle Diameter of 150 nm 30 g (288 mmol) of styrene (manufactured by FUJIFILM Wako Pure Chemical Corporation) and 3 g (42 mmol) of acrylic acid (manufactured by FUJIFILM Wako Pure Chemical Corporation) were suspended in 440 mL of ultrapure water, the solution was heated to 95° C., an aqueous solution obtained by dissolving 1 g of potassium persulfate (KPS) (manufactured by FUJIFILM Wako Pure Chemical Corporation) in 10 mL of ultrapure water was added thereto, and the resulting solution was stirred at 95° C. and 250 rpm for 6 hours. Thereafter, centrifugation was performed three times at 10,000 rpm for 6 hours, thereby obtaining latex particles. Finally, the obtained latex particles were redispersed in ultrapure water. Pure water was added thereto such that the concentration of solid contents reached 1% by mass, thereby preparing a diluted solution. The average particle diameter of the latex particles was 150 nm in a case of acquiring the diameter as a median size (d=50) measured at a temperature of 25° C. using a particle size analyzer FPAR-1000 (manufactured by Otsuka Electronics Co., Ltd.).

(2) Preparation of Fluorescent Latex Particles 100 mL of methanol was added to 100 mL of an aqueous dispersion liquid in which the concentration of solid contents of the latex particles with an average particle diameter of 150 nm, which had been prepared in the above-described manner, was 2% by mass, and the solution was stirred at room temperature for 10 minutes. In addition, 12 mg of a fluorescent dye (NK136, manufactured by Hayashibara Biochemical Laboratories Inc.) dissolved in 1 mL of N,N-dimethylformamide (DMF), 9 mL of $CHCl_3$, and 16 mg of ethanol, which had been separately prepared, was slowly added dropwise to the latex solution over 60 minutes. After the dropwise addition was completed, the organic solvent was distilled off under reduced pressure with an evaporator, centrifugation and redispersion in a phosphate buffered saline (PBS) aqueous solution were repeated three times, and purification was performed, thereby preparing fluorescent latex particles.

(3) Preparation of Monoclonal Antibody

An anti-SAA monoclonal antibody (Anti-SAA) and an anti-CRP (C-reactive protein) monoclonal antibody were prepared in the following manner using a mouse ascites method.

Spleen cells were extracted after mice were immunized with SAA purchased from Hytest Ltd., and mixed with myeloma (product name: P3-X63-Ag8-U1, manufactured by Cosmo Bio Co., Ltd.), and cell fusion was performed by a polyethylene glycol (PEG) method. As the cells used, the spleen cells collected after 3 days from the final immunization were used. The ratio of the spleen cells to myeloma (spleen cells:myeloma) was set to 10:1. Cell seeding was carried out by seeding the spleen cells in a 96-well plate at 0.5 to $1.0\times10^5$ cells/well. As the medium used, RPMI-1640 (Roswell Park Memorial Institute medium), 10% FBS (fetal bovine serum), and HAT (hypoxanthine-aminopterin-thymidine mixed medium) were used as appropriate. The fused cells (hybridomas) which had been finally proliferated were injected into the abdominal cavities of mice, and ascites was taken out after a certain period of time, and the resultant obtained by performing centrifugation and the purification steps was collected as an anti-SAA monoclonal antibody (Anti-SAA). Further, an anti-CRP monoclonal antibody was prepared using CRP (manufactured by Oriental Yeast Co., Ltd.) purified from a culture solution of Escherichia coli in the same manner as the preparation of the anti-SAA monoclonal antibody.

(4) Preparation of Fluorescent Latex Particles Modified with Anti-SAA Antibody

Fluorescent particles modified with anti-SAA antibody were prepared as follows.

88 μL of a 50 mmol/L MES (2-(N-morpholino) ethanesulfonic acid) buffer (pH of 6.6) solution was added to 275 μL of a 2 mass % (concentration of solid contents) fluorescent latex particle aqueous solution (average particle diameter of 150 nm), 176 μL of a 5 mg/mL anti-SAA monoclonal antibody (Anti-SAA) was added thereto, and the solution was stirred at room temperature for 15 minutes. Thereafter, 5 μL of a 10 mg/mL EDC (1-ethyl-3-(3-dimethylaminopropyl) carbodiimide hydrochloride, manufactured by FUJIFILM Wako Pure Chemical Corporation) aqueous solution was added thereto, and the solution was stirred at room temperature for 2 hours. After 8.8 μL of a 2 mol/L Glycine (manufactured by FUJIFILM Wako Pure Chemical Corporation) aqueous solution was added thereto and the solution was stirred for 15 minutes, centrifugation (15000 rpm, 4° C., 15 minutes) was performed to precipitate fluorescent latex particles. Thereafter, the supernatant was removed, 500 μL of a PBS solution (pH of 7.4) was added thereto, and the fluorescent latex particles were redispersed with an ultrasonic washing machine. After centrifugation (15000 rpm, 4° C., 15 minutes) was performed again to remove the supernatant, 500 μL of a PBS (pH of 7.4) solution containing 1% by mass of BSA was added thereto to redisperse the fluorescent latex particles, thereby preparing a 1 mass % solution of anti-SAA antibody-bound fluorescent latex particles.

(5) Preparation of Latex Particles Modified with Anti-CRP Antibody without Fluorescent Labeling 96 μL of a 250 mmol/L MES buffer (pH of 5.6) solution and 25 mL of ultrapure water were added to 300 μL of a 2 mass % (concentration of solid contents) latex particle aqueous solution (average particle diameter of 150 nm), and 182 μL of a 5 mg/mL anti-CRP monoclonal antibody was added thereto. The obtained mixture was stirred at room temperature for 15 minutes. Thereafter, 9.6 μL of a 10 mg/mL EDC (N-ethyl-N'-(3-dimethylaminopropoxy) carbodiimide) aqueous solution was added thereto, and the obtained mixture was stirred at room temperature for 2 hours. 30 μL of a 2 mol/L glycine (manufactured by FUJIFILM Wako Pure Chemical Corporation) aqueous solution was added thereto, the obtained mixture was stirred for 30 minutes, and centrifugation (15000 rpm, 4° C., 15 minutes) was performed to precipitate latex particles. The supernatant was removed, 600 μL of a PBS solution (pH of 7.4) was added to the precipitate, and latex particles were redispersed with an ultrasonic washing machine. After centrifugation (15000 rpm, 4° C., 15 minutes) was performed again to remove the supernatant, 600 μL of a PBS (pH of 7.4) solution containing 1% by mass of BSA was added to the precipitate, and the latex particles were redispersed. In this manner, a 1 mass % solution of anti-CRP antibody-bound latex particles was prepared.

(6) Preparation of Dry Particles

240 μL of ultrapure water, 417 μL of a 20 mass % sucrose aqueous solution, 229 μL of a 20 mass % BSA aqueous solution, 125 μL of a dispersion liquid containing 1% by mass of the fluorescent latex particles (average particle diameter of 150 nm) prepared in the section of (4) and modified by an anti-SAA antibody, and 899 μL of a 0.8 mol/L MES buffer solution (pH=6.5) were mixed. A cup using polypropylene (Prime Polypro random PP grade, manufactured by Prime Polymer Co., Ltd.) as a base was prepared, and 40 μL of the above-described mixed solution was spotted in the cup. Thereafter, the solution was dried for 24 hours using a Super Dry Dryer (Ultra Super Dry 00 Series, manufactured by Toyo Living Co., Ltd.) until the moisture content was set to 12% or less, and the resultant was stored in an environment of 25° C. and 50% RH (relative humidity) for 15 days, thereby preparing dry particles used in Example 1 listed in Table 1. Further, in the preparation of dry particles used in Example 2 and Comparative Example 4 described below, dry particles were prepared in the same manner as described above except that the latex particles modified with the anti-CRP antibody without the fluorescent labeling which were prepared in the above-described manner were mixed 5 times the mass of the anti-SAA antibody-modified fluorescent latex particles.

(7) Preparation of Substrate

A gold film used as a test area and a gold film used as a control area next to the gold film were prepared on one surface of a substrate using polymethylmethacrylate (PMMA, ACRYPET VH-001, manufactured by Mitsubishi Rayon Co., Ltd.) as a base according to a magnetron sputtering method such that the width of both the test area and the control area was set to 4 mm and the thickness thereof was set to 36 nm. The substrate was cut into a width of 5 mm to prepare a substrate. A liquid (concentration: 10 μg/mL in 150 mmol NaCl) containing an anti-SAA monoclonal antibody was spotted on the gold film in the test area of the substrate, and the substrate was incubated at 25° C. for 1 hour so that the liquid was physically adsorbed for immobilization.

(8) Washing and Blocking of Substrate

Before the substrate prepared in the above-described manner was attached to a flow path of a sensor chip, the substrate was repeatedly washed three times using 300 μL of a washing solution (a PBS solution (pH of 7.4) containing 0.05% by mass of Tween (registered trademark) 20 (polyoxyethylene (20) sorbitan monolaurate, manufactured by FUJIFILM Wako Pure Chemical Corporation)) prepared in advance. After completion of washing, 300 μL of a PBS solution (pH of 7.4) containing 1% by mass of casein (manufactured by Thermo Scientific Inc.) was added thereto to perform blocking of a non-adsorbed portion of the antibody on the gold film, and the substrate was allowed to stand at room temperature for 1 hour. After the substrate was washed with the above-described washing solution, 300 μL of Immunoassay Stabilizer (manufactured by ABI) was added thereto as a stabilizer, the substrate was allowed to stand at room temperature for 30 minutes, and the solution was removed and the moisture was completely removed using a dryer.

(9) Preparation of Sensor Chip

Figure 2:
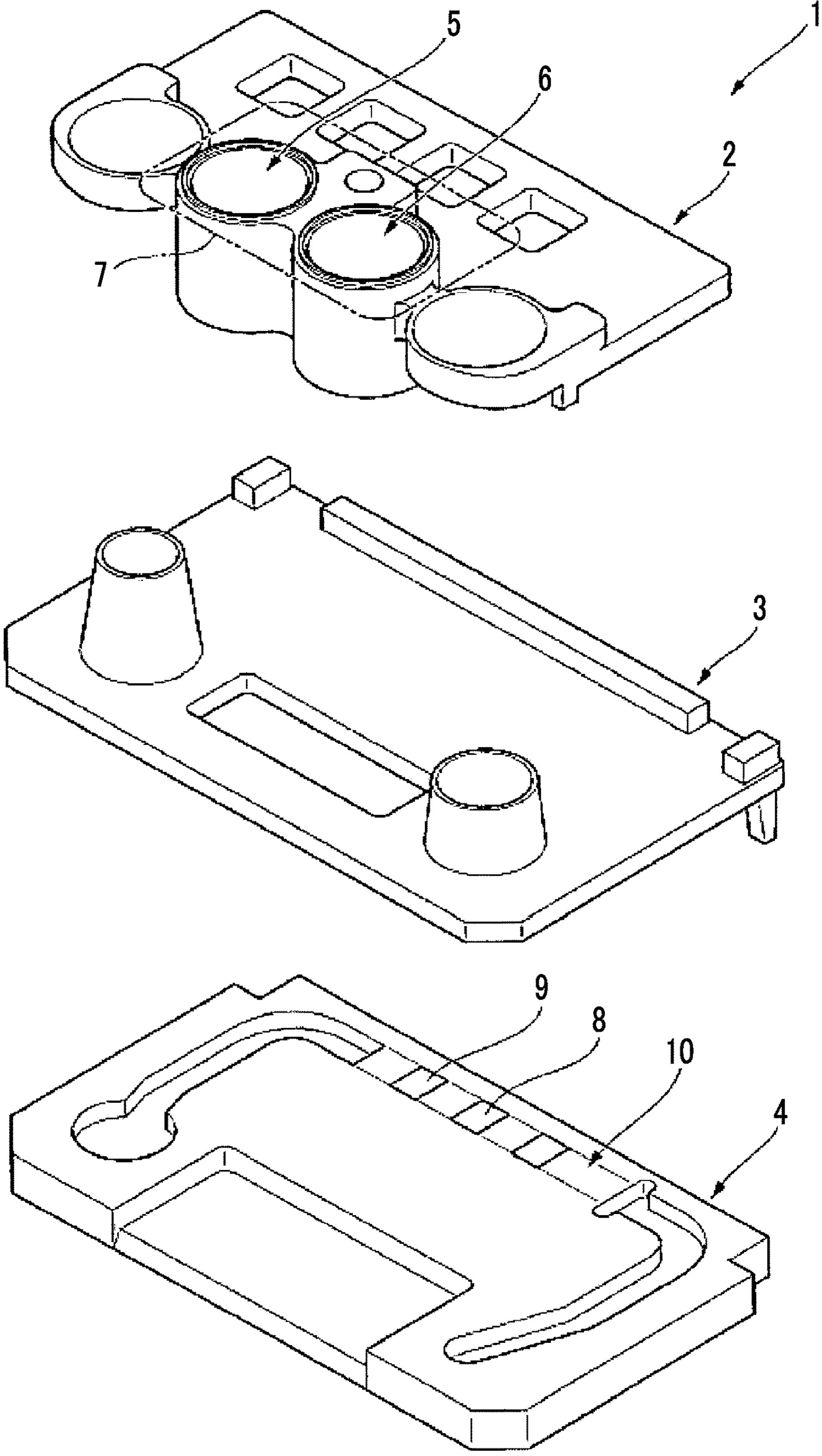
FIG. 2 is an exploded view of a sensor chip.

The prepared substrate was enclosed in the flow path so as to have the configuration of the second embodiment described in JP2010-190880A, thereby preparing a flow path type sensor chip. FIG. 1 and FIG. 2 illustrate the schematic views thereof. FIG. 1 is a schematic view of a sensor chip 1, and FIG. 2 is an exploded view of the sensor chip 1. The sensor chip 1 includes an upper member 2, an intermediate member 3, and a substrate 4. The upper member 2 is provided with a first container 5 and a second container 6. Further, the first container 5 and the second container 6 are collectively referred to as a container group 7. A flow path 10 is formed on the substrate 4, and a detection region 8 and a reference region 9 are formed on the flow path 10.

(10) Preparation of Test Sample

As the serum of a cat, the serum of a crossbreed purchased from Kitayama Labes Co., Ltd. was used, and test samples (specimens) No. 1 and No. 2 with different concentrations of serum amyloid A as the test substances were prepared.

(11) Measurement According to Control Method

In the immunoassay, the concentration of SAA in each of the test samples No. 1 and No. 2 prepared in the section (10) was measured according to the instruction manual using an ELISA kit (Phase SAA Assay (cat. no. TP-802): Control kit, manufactured by Tridelta) used by those skilled in the art. The concentrations of SAA in the test samples No. 1 and No. 2 were respectively 20.0 μg/mL and 80.1 μg/mL.

(12) Immunoassay of SAA using Fluorescent Particles

10 μL of the test sample (serum of a cat) No. 1 prepared in the section of (10) was weighed and sufficiently mixed with 90 μL of a physiological saline solution containing 0.33% by mass of n-dodecyl-β-D-maltoside (product name: D316, manufactured by Dojindo Co., Ltd.) serving as a nonionic surfactant, thereby preparing a mixed solution 1 of the test sample. The concentration of the surfactant D316 in the mixed solution was 0.30% by mass. Next, the prepared mixed solution 1 was added to the cup dried by spotting the anti-SAA antibody-labeled fluorescent particles prepared in the section of (4), and the solution was sufficiently stirred for 10 minutes. Next, the mixed solution 1 mixed with the fluorescent particles was spotted on an injection port of the flow path type sensor chip obtained by enclosing the substrate prepared in the above-described manner. After the spotting, the mixed solution 1 was allowed to flow down onto the flow path at a rate of 10 μL/min while pump suction was performed, and the fluorescence intensity on the surface of the gold film on which the SAA antibody was fixed was continuously measured for 1.5 minutes. The rate of an increase in the fluorescence signal value of the fluorescence intensity obtained in each substrate per unit time was acquired. The rate of an increase in the fluorescence signal value per unit time was acquired with respect to the test sample No. 2 in the same manner as described above. The results are listed in Table 1. The "signal value" in Table 1 indicates the "rate of increase in signal value".

Example 2

The rate of an increase in the fluorescence signal value was acquired with respect to each of the test samples No. 1 and No. 2 in the same manner as in Example 1 except that the surfactant was changed to n-decyl-β-D-maltoside (trade name: D382, manufactured by Dojindo Co., Ltd.) in place of D316 in Example 1.

Comparative Examples 1 to 7

The rate of an increase in the fluorescence signal value was acquired with respect to each of the test samples No. 1 and No. 2 in the same manner as in Example 1 except that the surfactant in Example 1 was changed to the surfactant listed in Table 1.

(13) Creation of Calibration Curve

Next, the serum of a crossbreed purchased from Kitayama Labes Co., Ltd. was used, and test samples (specimens) No. 3 to No. 7 with different concentrations of the test substances were prepared. In a case where the concentrations of SAA were measured by performing the measurement according to the control method described in the section of (11), the concentrations thereof were respectively 2.9 μg/mL, 5.5 μg/mL, 60.8 μg/mL, 111.0 μg/mL, and 159.1 μg/mL. Using the test samples (specimens) No. 3 to No. 7, the signals of the test samples (specimens) No. 3 to No. 7 were respectively measured using the kits described in Examples 1 and 2 and Comparative Examples 1 to 7, and the calibration curves were respectively created for the kits described in Examples 1 and 2 and Comparative Examples 1 to 7.

(14) Measurement of Multi-Specimen Correlation

With respect to 500 specimens of various kinds of cat serums obtained from collected blood in an animal hospital, the signals of the specimens were respectively measured using the kits described in Examples 1 and 2 and Comparative Examples 1 to 7, the concentrations of SAA were respectively calculated from the calibration curves created in the section of (13), and the evaluation results of the correlation between the concentrations and the known concentrations measured by the control method described in the section of (11) are listed in Tables 1 and 2 as the results of the "multi-specimen correlation". In Tables 1 and 2, the signal value (20) indicates a signal value at a SAA concentration of 20 μg/mL, and the signal value (80) indicates a signal value at a SAA concentration of 80 μg/mL.

TABLE 1

| | Example 1 | Example 2 | Comparative Example 1 | Comparative Example 2 | Comparative Example 3 |
|---|---|---|---|---|---|
| Surfactant | Dodecyl maltoside | Decyl maltoside | Octyl maltoside | Laureth 10 | Laureth 10 |
| Molecular weight | 511 | 483 | 455 | 627 | 1067 |
| HLB | 17.4 | 19.0 | 21.1 | 12.4 | 14.9 |
| Signal value (20) | 617 | 1600 | 207 | 288 | 50 |
| Signal value (80) | 1601 | 2914 | 190 | 810 | 120 |
| Evaluation of signal intensity | A | A | C | B | C |
| Evaluation of multi-specimen correlation | A | A | — | A | — |

TABLE 2

| | Comparative Example 4 | Comparative Example 5 | Comparative Example 6 | Comparative Example 7 |
|---|---|---|---|---|
| Surfactant | Laureth 30 | Glycerin 5-12 alkyl ester | Glycerin 5-14 alkyl ester | Glycerin 6-8 alkyl ester |
| Molecular weight | 1508 | 571 | 599 | 589 |
| HLB | 15.9 | 13.7 | 12.8 | 16.5 |
| Signal value (20) | 20 | 278 | 123 | 517 |
| Signal value (80) | 54 | 350 | 205 | 340 |
| Evaluation of signal intensity | C | C | C | C |
| Evaluation of multi-specimen correlation | — | — | — | — |

<Evaluation Standards for Signal Intensity>

A: Satisfactory (the signal value at a SAA concentration of 20 μg/mL was 300 or greater, and the signal value at a SAA concentration of 80 μg/mL was 1200 or greater)

B: Relatively satisfactory (the signal value at a SAA concentration of 20 μg/mL was 100 or greater, the signal value at a SAA concentration of 80 μg/mL was 400 or greater, and the A region was excluded)

C: Insufficient (the signal value at a SAA concentration of 20 μg/mL was less than 100, and the signal value at a SAA concentration of 80 μg/mL was less than 400)

<Evaluation Standards for Multi-Specimen Correlation>

A: Satisfactory (a correlation coefficient R of the linear approximation line of the correlation plot between the SAA measurement values of 500 specimens according to the present invention and the SAA measurement values measured by the control method was 0.90 or greater)

B: Relatively satisfactory (the correlation coefficient R of the linear approximation line of the correlation plot between the SAA measurement values of 500 specimens according to the present invention and the SAA measurement values measured by the control method was greater than or equal to 0.80 and less than 0.90)

C: Insufficient (the correlation coefficient R of the linear approximation line of the correlation plot between the SAA measurement values of 500 specimens according to the present invention and the SAA measurement values measured by the control method was less than 0.80)

D: Since the signal intensity was weak and the calibration curve was not able to be created, the quantification was not able to be performed.

Since the signal intensity was weak and the calibration curve was not able to be created, the quantification was not able to be performed.

As listed in Tables 1 and 2, it was confirmed that in a case where a nonionic surfactant having an HLB value of 17 to 20 and a molecular weight of 1000 or less is used as a surfactant and the kit contains a buffer capable of adjusting the pH of the reaction solution to be in a range of 5.5 to 7.0 or a range of 8.5 to 9.0, the signal intensity and the multi-specimen correlation (correlation) which are the effects of the present invention are satisfactory.

Examples 3 to 6 and Comparative Examples 8 to 10

Samples of Examples 3 to 6 and Comparative Examples 8 to 10 were prepared in the same manner as in Example 1 except that the buffer listed in Table 3 was used in place of 899 μL of a 0.8 mol/L MES buffer solution (pH=6.5) used in Example 1 and the pH was adjusted to be the pH listed in Table 3. The sample of Comparative Example 8 was prepared by changing 899 μL of a 0.8 mol/L MES buffer solution (pH=6.5) in Example 1 to ultrapure water. Further, the pH listed in Table 3 indicates the pH of the reaction solution in a case where the specimen was dispensed into the cup of the cartridge and the dried reagent in the cup was sufficiently stirred so as to be completely dissolved therein. Since the sample of Comparative Example 8 did not contain a buffer, the pH thereof was assumed to be a value reflecting the pH of serum. The calibration curves for the samples of Examples 3 to 6 and Comparative Examples 8 to 10 were respectively acquired according to the method described in the section of (13).

(15) Measurement of High-Value Deviation Specimen

Further, the measurement results obtained by acquiring the SAA values from the calibration curves for the specimen (one specimen) which has a concentration of less than 20 μg/mL that is considered to be the reference range of cat SAA among the 500 specimens used in the measurement of the multi-specimen correlation described in the section of (14) and in which the measurement value in Comparative Example 8 is high and deviated most from the measurement value according to the control method, using the kits of Examples 1, 3, and 6 and Comparative Examples 8 to 10, are listed in Table 3. The measurement values measured by the control method are also listed in Table 3 (the columns of the control method).

TABLE 3

| | Example 3 | Example 1 | Example 4 | Comparative Example 8 | Comparative Example 9 | Comparative Example 10 | Example 5 | Example 6 | Control method |
|---|---|---|---|---|---|---|---|---|---|
| Buffer | MES | MES | HEPES | None | BICINE | BICINE | BICINE | BICINE | — |
| pH | 5.5 | 6.5 | 7 | 7.7 | 7.5 | 8 | 8.5 | 9 | — |
| Measurement value (μg/mL) | 1 | 5 | 17 | 96 | 71 | 30 | 5 | 1 | 1 |

As listed in Table 3, it was confirmed that the high-value deviation which is the effect of the present invention is improved to be in a target range in the buffer pH range of the present invention in a case where the concentration of cat SAA is a target value (20 μg/mL or less) assuming that the reference value thereof is 20 μg/mL.

EXPLANATION OF REFERENCES

1: sensor chip
2: upper member
3: intermediate member
4: substrate
5: first container
6: second container
7: container group
8: detection region
9: reference region
10: flow path

What is claimed is:

1. A reagent kit for measuring serum amyloid A, comprising:

first particles having a label and modified with a first binding substance having a property of specifically binding to serum amyloid A;

at least one nonionic surfactant having a hydrophilic-lipophilic balance value of 17 to 20, which is defined by (inorganicity value/organicity value)×10, and a molecular weight of 1000 or less; and a buffer adjusting a pH of a reaction solution to be in a range of 5.5 to 7.0 or a range of 8.5 to 9.0.

2. The reagent kit according to claim 1, wherein an average particle diameter of the first particles is in a range of 70 nm to 500 nm.

3. The reagent kit according to claim 1, further comprising:

second particles which are modified with a second binding substance having no property of specifically binding to serum amyloid A and do not have a label.

4. The reagent kit according to claim 3, wherein an average particle diameter of the second particles is in a range of 70 nm to 500 nm.

5. The reagent kit according to claim 1, wherein the label includes a fluorescent dye.

6. The reagent kit according to claim 1, wherein the serum amyloid A is serum amyloid A in cat serum or cat plasma.

7. The reagent kit according to claim 1, wherein the buffer is 2-(N-morpholino) ethanesulfonic acid or N,N-bis(2-hydroxyethyl)glycine.

8. The reagent kit according to claim 1, wherein the first binding substance is an antibody.

9. A measurement kit for serum amyloid A, comprising:

the reagent kit according to claim 1; and a substrate on which a first metal film is formed, and a third binding substance having a property of specifically binding to serum amyloid A or of specifically binding to the first binding substance is fixed to the first metal film.

10. The measurement kit according to claim 9, wherein a second metal film is further formed on the substrate and a fourth binding substance having a property of specifically binding to the first binding substance, but not having a property of binding to serum amyloid A is fixed to the second metal film.

11. A measurement kit for serum amyloid A, comprising:

the reagent kit according to claim 2; and a substrate on which a first metal film is formed, and a third binding substance having a property of specifically binding to serum amyloid A or of specifically binding to the first binding substance is fixed to the first metal film.

12. A measurement kit for serum amyloid A, comprising:

the reagent kit according to claim 3; and a substrate on which a first metal film is formed, and a third binding substance having a property of specifically binding to serum amyloid A or of specifically binding to the first binding substance is fixed to the first metal film.

13. A measurement kit for serum amyloid A, comprising:

the reagent kit according to claim 4; and a substrate on which a first metal film is formed, and a third binding substance having a property of specifically binding to serum amyloid A or of specifically binding to the first binding substance is fixed to the first metal film.

14. A measurement kit for serum amyloid A, comprising:

the reagent kit according to claim 5; and a substrate on which a first metal film is formed, and a third binding substance having a property of specifically binding to serum amyloid A or of specifically binding to the first binding substance is fixed to the first metal film.

15. A measurement kit for serum amyloid A, comprising:

the reagent kit according to claim 6; and a substrate on which a first metal film is formed, and a third binding substance having a property of specifically binding to serum amyloid A or of specifically binding to the first binding substance is fixed to the first metal film.

16. A measurement kit for serum amyloid A, comprising:

the reagent kit according to claim 7; and a substrate on which a first metal film is formed, and a third binding substance having a property of specifically binding to serum amyloid A or of specifically binding to the first binding substance is fixed to the first metal film.

17. A measurement kit for serum amyloid A, comprising:

the reagent kit according to claim 8; and a substrate on which a first metal film is formed, and a third binding substance having a property of specifically binding to serum amyloid A or of specifically binding to the first binding substance is fixed to the first metal film.

18. A measurement method for serum amyloid A in a biological sample, the method comprising:

a step of preparing a mixed solution which contains a biological sample containing serum amyloid A, first particles having a label and modified with a first binding substance having a property of specifically binding to serum amyloid A, at least one nonionic surfactant having a hydrophilic-lipophilic balance value of 17 to 20, which is defined by (inorganicity value/organicity value)×10, and a molecular weight of 1000 or less, and a buffer adjusting a pH of a reaction solution to be in a range of 5.5 to 7.0 or a range of 8.5 to 9.0;

a step of adding the mixed solution to an injection port at one end of a substrate on which a first metal film on which a third binding substance having a property of specifically binding to serum amyloid A is fixed is formed;

a step of allowing the mixed solution to flow down onto the substrate; and a step of acquiring information of the label on the first metal film.

19. The measurement method for serum amyloid A according to claim 18, wherein in a case where the mixed solution is prepared, the biological sample is diluted with physiological saline at a dilution ratio of 4 times to 100 times.

* * * * *